United States Patent [19]
Brazeau

[11] Patent Number: 5,843,123
[45] Date of Patent: Dec. 1, 1998

[54] CUTANEOUS HARNESS FOR SUTURELESS WOUND CLOSING

[75] Inventor: Paul Brazeau, Montréal, Canada

[73] Assignee: Theratechnologies Inc., Montreal, Canada

[21] Appl. No.: 706,638

[22] Filed: Sep. 6, 1996

Related U.S. Application Data

[63] Continuation of Ser. No. 319,116, Oct. 6, 1994, abandoned.

[51] Int. Cl.$^6$ .................................................. A61B 17/08
[52] U.S. Cl. ........................... 606/213; 606/215; 606/216
[58] Field of Search .................................. 606/212–213, 606/215–218

[56] References Cited

U.S. PATENT DOCUMENTS

| | | |
|---|---|---|
| 345,541 | 7/1886 | Reichardt . |
| 1,428,495 | 9/1922 | Radcliffe . |
| 1,774,489 | 10/1930 | Sarason . |
| 2,303,131 | 11/1942 | Morgan . |
| 2,387,131 | 10/1945 | Fernandez . |
| 2,752,921 | 7/1956 | Fink . |
| 3,983,878 | 10/1976 | Kawchitch . |
| 4,637,380 | 1/1987 | Orejola .................................. 606/216 |
| 4,702,251 | 10/1987 | Sheehan ................................. 606/216 |
| 4,742,826 | 5/1988 | McLorg ................................. 606/215 |
| 4,754,758 | 7/1988 | Li .......................................... 606/213 |
| 5,176,703 | 1/1993 | Peterson ................................ 606/216 |
| 5,730,743 | 3/1998 | Kirsch et al. ............................ 606/69 |

FOREIGN PATENT DOCUMENTS

| | | |
|---|---|---|
| 2 253 491 | 7/1975 | France . |
| 2 268 504 | 11/1975 | France . |
| 111345 | 10/1899 | Germany . |
| 111 345 | 6/1900 | Germany . |
| 692496 | 7/1965 | Italy . |
| 927236 | 5/1982 | U.S.S.R. ................................. 606/218 |
| WO 90/12912 | 11/1990 | WIPO . |

Primary Examiner—Michael Buiz
Assistant Examiner—Tina T. D. Pham
Attorney, Agent, or Firm—Klauber & Jackson

[57] ABSTRACT

The present invention relates to a device for closing cutaneous wounds without sutures, which comprises a pair of three-dimensionally flexible strips adopted to be positioned on each side of a wound and formed of a plurality of laterally spaced apart elongated anchoring members extending side-by-side in succession and transversely of the wound and being interconnected in a three-dimensionally flexible manner to follow the lips of an open wound. Each of the anchoring members has on the underside thereof an adhesive surface for adhesion directly of indirectly to the skin of a patient, and includes at an inner end thereof a thread receiving and retaining portion, whereby a thread can be engaged lace-wise through the anchoring members of both strips so as to draw the anchoring members of one strip towards the anchoring members of the other strip in such a way so as to close in a constant tensiometric way the open wound extending between the two strips with the lips of the wound being equidistant along the entire length thereof.

23 Claims, 6 Drawing Sheets

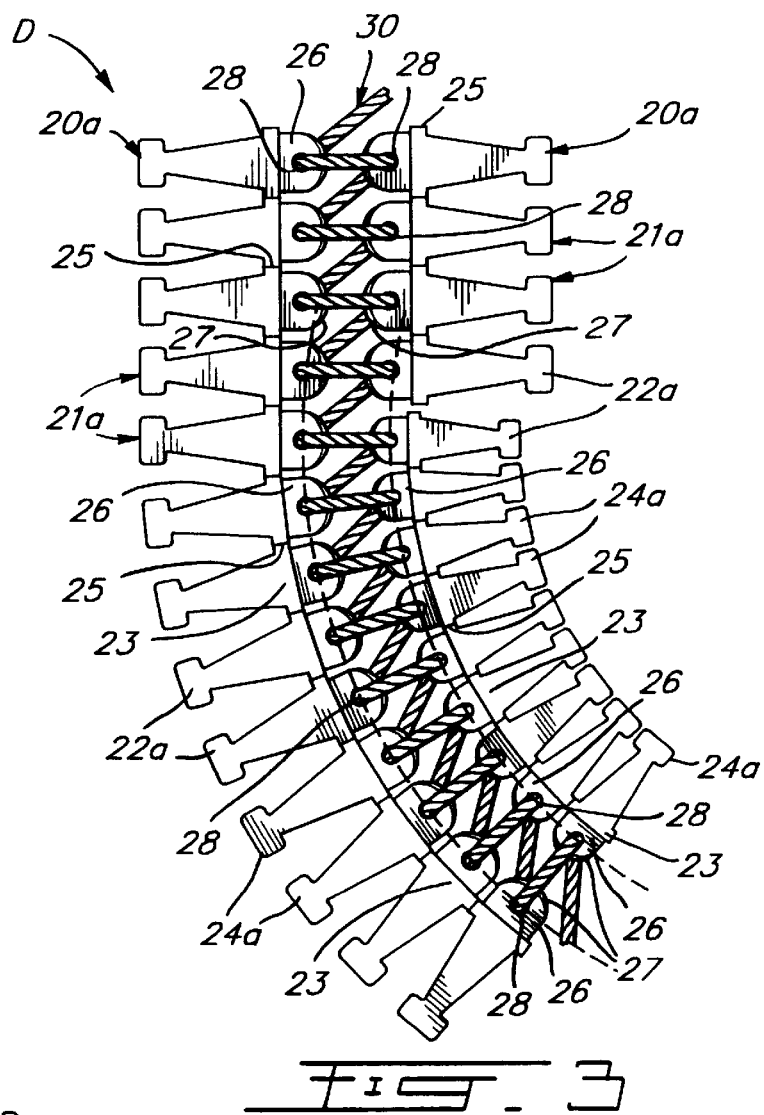
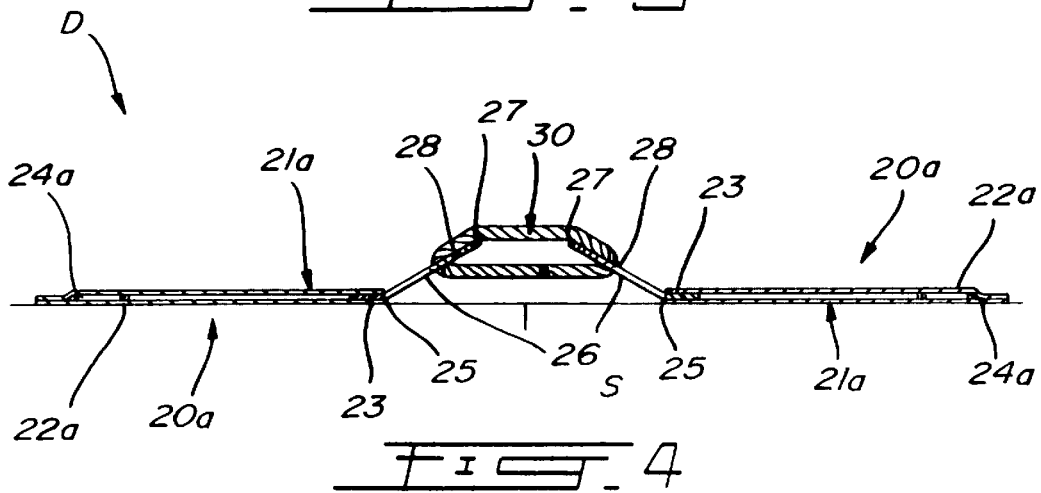

 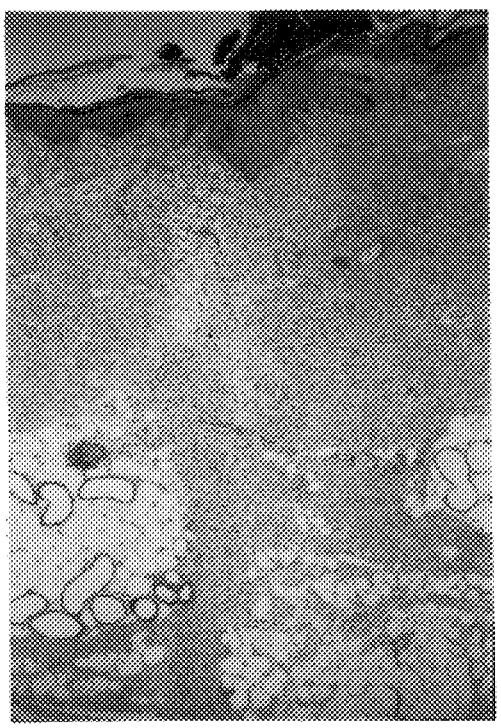
HARNESS FIG. 9A  SUTURES FIG. 9B

CUTANEOUS HARNESS FOR SUTURELESS WOUND CLOSING

This application is a continuation of application Ser. No. 08/319,116, filed Oct. 6, 1994, abandoned.

BACKGROUND OF THE INVENTION (a) Field of the Invention

The invention relates to a cutaneous harness for wound closing without sutures, and therefore without any perforation of the skin adjacent to the wound.

(b) Description of Prior Art

The body's first lines of defense against infection are the barriers offered by surfaces exposed to the external environment. Very few microorganisms can penetrate the intact skin. Once invaders gain entry into the skin, it disturbs inflammation, the response to injury. The local manifestations of the inflammatory response are a complex sequence of highly interrelated events, the overall functions of which are to bring neutrophils and phagocytes into the damaged area so that they can destroy (or inactivate) the foreign invaders and set the stage for tissue repair. The sequence of events which constitute the inflammatory response varies, depending upon the injurious agent (bacteria, cold, heat, trauma, etc.), the site of injury, and the state of the body. It should be emphasized that inflammation, in its most basic form, is the nonspecific innate response to foreign material.

Wound healing is a complex cascade of cellular and biochemical events which lead to wound closure and repair of tissues. Three successive phases are classically distinguished in this process:

1) the inflammatory phase, corresponding to increased vascular permeability and migration of neutrophils, leukocytes and macrophages;

2) the proliferative phase, characterized by fibroblast proliferation and collagen synthesis, resulting in granulation tissue formation; and 3) the remodeling phase, where collagen and granulation tissue rearrangements results in scar resorption.

Sutures are well known to involve tying adjacent lips of wound together at intervals along the length of the wound. This provides an unsatisfactory closure of the wound because the epithelium cells of the skin of the adjacent lips are, at intervals, either in too close proximity or too distant from one another for adequate healing of the wound. Furthermore, sutures, although they are efficient in closing a wound, perforate the skin adjacent to the wound site and cause micro-inflammatory responses adjacent to the wound site. There are great advantages in providing a means to close a wound without causing this undesired micro-inflammation adjacent to the wound site.

Various types of appliances have previously been proposed for providing sutureless closure of surgical incisions. For example, U.S. Pat. Nos. 345,541, 1,428,495, 1,774,489, and 2,387,131 and Italian Patent No. 692,496 disclose adhesive members which are joined together by suitable lacing which can be tightened. All these devices are flexible in two-dimension only and cannot follow the edges of transversely non-linear or curved wounds. Thus, these devices cannot ensure the adequate closure of nonlinear wounds.

In U.S. Pat. No. 2,752,921 there is disclosed essentially an adhesive tape formed in two halves which may be brought together by a zip fastener among others. The wound edges must follow the line of the fastener very accurately if the skin edges are to be brought together correctly by closure of the fastener. Moreover a zip fastener does not produce a sufficient closing action to ensure that the skin edges are brought together and held immobile relative to one another. Again, this device is not flexible in the plan of the wound and cannot follow non-linear lips of a curved wound.

U.S. Pat. No. 3,983,878 discloses an appliance which enables the closure of a surgery wound to be made very rapidly and which may be designed to ensure minimum movement of the skin edges relative to one another. This appliance consists in a tape member which has an adhesive surface for fastening to the skin of a surgery patient and a series of parallel ribs defining a course along which an incision through the tape and the skin beneath can be made. This appliance also includes a spring closure member applicable to ribs of the tape member and to be clasped in a closed position for wound closure. This appliance is designed to be used in surgical procedures to produce linear incisions. This appliance is not flexible in the plan of the incision and cannot provide for adequate closure of non-linear incisions.

German Patent No. 111,345 describes a strip having one longitudinal part being adhesive and another longitudinal part attached thereto being provided with lacing means. The adhesive portion of the strip is formed of a plurality of teeth which seems to be flexible in three-dimension but the lacing portion is formed of one-piece only and cannot be flexed to follow a curved wound.

None of these methods ensures that the nonlinear lips of a curved skin wound will be held together properly and at an appropriate distance for healing of the wound to occur.

It would be highly desirable to provide a sutureless closure means which would be flexible in three-dimension and which would allow for an isotensiometric closure of curved or straight wounds. Such an isotensiometric closure of wounds would permit for the rapid healing of wounds, and hence, recovery of patients at a faster rate and with less infection wound problems and scaring side effects.

Moreover, none of the appliances of the prior art ensures the visibility of the wound and its access once held in a closed position. Also, none of the appliances of the prior art allows for the rapid access to the wound in case of an emergency.

SUMMARY OF THE INVENTION

One aim of the present invention is to provide a sutureless wound closure device which is flexible in three-dimension and which allows for an isotensiometric closure of curved or straight wounds.

Another aim of the present invention is to provide a sutureless wound closure device which allows for a quick and easy closure of a wound without the need for local anesthesia.

Another aim of the present invention is to provide a sutureless wound closure device which also allows for the inspection of the wound by the clinicians or for the delivery of medication to the wound while the lips are held closed by the device.

Another aim of the present invention is to provide rapid access to the wound in case of an emergency, where easy undressing and subsequent reclosing of the sutureless wound closure device is possible with the same efficiency.

In accordance with the present invention there is provided a device for closing cutaneous wounds comprising at least a pair of three-dimensionally flexible strips each formed of a plurality of anchoring means disposed side-by-side and interconnected to one another in a three-dimensionally flexible manner so that the strips can outwardly follow the lips of an open wound, attachment means being provided for detachably securing to the skin of a patient at least one of the strips on each side of the wound with the anchoring means being adapted to extend substantially transversely of the wound, the anchoring means on both sides of the wound being adapted to receive a thread so as to draw in a substantially lace-like way the anchoring means of each side of the wound towards the wound thereby substantially closing the wound.

Also in accordance with the present invention, there is provided a device for closing cutaneous wounds comprising at least a pair of flexible strips each formed of a plurality of anchoring means disposed side-by-side and interconnected to one another in a flexible manner so that the strips can outwardly follow the lips of an open wound, attachment means being provided for detachably securing to the skin of a patient at least one of the strips on each side of the wound with the anchoring means being adapted to extend substantially transversely of the wound, the anchoring means on both sides of the wound being adapted to receive a thread so as to draw in a substantially lace-like way the anchoring means of each side of the wound towards the wound thereby substantially closing the wound with the anchoring means being adapted for exerting a substantially constant tensiometric pressure substantially along the entire length of the wound.

Further in accordance with the present invention, there is provided a device for closing cutaneous wounds comprising at least a pair of flexible strips each formed of a plurality of anchoring means disposed side-by-side and interconnected to the wound in a flexible manner so that the strips can follow the lips of an open wound outwardly thereof, attachment means being provided for detachably securing to the skin of a patient at least one of the strips on each side of the wound with the anchoring means being adapted to extend substantially transversely of the wound, the anchoring means on both sides of the wound being adapted to receive a thread so as to draw in a substantially lace-like way the anchoring means of each side of the wound towards one another thereby substantially closing the wound.

BRIEF DESCRIPTION OF THE DRAWINGS

Having thus generally described the nature of the invention, reference will now be made to the accompanying drawings, showing by way of illustration a preferred embodiment thereof, and wherein:

FIG. 3 is a top plan view of a first sutureless wound closure device in accordance with the present invention which includes a pair of strips in accordance with a second embodiment thereof which is similar to that of FIG. 2, the pair of strips being fastened together using a thread in a typical operative position;

FIG. 4 is an end elevational view of the sutureless wound closure device of FIG. 3 fastened together in a typical operative position;

FIGS. 9A and 9B illustrates the morphometric analysis of 7 day-old wounds in accordance with the present invention compared to sutures.

DETAILED DESCRIPTION OF THE INVENTION

A sutureless wound closure device in accordance with the present invention provides for a wound closure without sutures, and thus without any foreign material in close proximity to the wound site. Such a sutureless closure of wound diminishes greatly the risks of wound contamination or infection.

Figure 1:
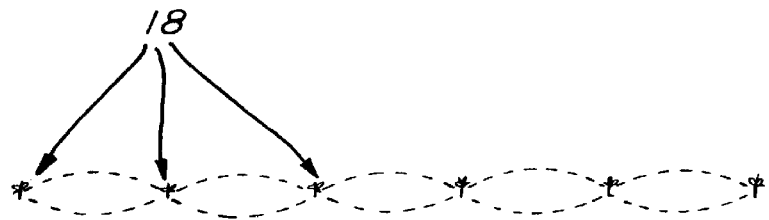
FIG. 1 is a schematic top plan view of a wound closure using prior art sutures.

The sutureless wound closure device of the present invention is flexible in three-dimension and can follow the contour or the edges of the lips of a curved wound. More importantly, this device allows for a isotensiometric closure of a wound, as the two adjacent lips of a wound are brought in close proximity to one another and spaced apart at the same fixed distance from each another along the entire length of the wound, regardless whether the wound is curved, linear or both. This isotensiometric closure of the wounds provide for an optimum healing process where the blood flow and migration of cells are greatly facilitated by a constant spacing. The isotensiometric closure of the wound results in minimum scarring once it is healed. With reference to FIG. 1, sutures on the other hand provide for a closure of wounds wherein the lips of a wound touch each other tightly at suture sites 18, at intervals, and in between the suture sites 18 the wound lips are spaced apart from each other. When lips are too tightly held one against another, it prevents blood flow to the wound site for an harmonious healing process to occur, where all the biochemical steps are synchronized. Thus, the device of the present invention overcomes all of the drawbacks of the closure devices of the prior art, by allowing for the wound to be closed without sutures and wherein the adjacent lips of a wound are kept at a constant spacing along the entire length of the wound for an optimum healing of the wound.

The sutureless wound closure device of the present invention does not require the use of local anesthesia or of haemostatic pliers. Haemostatic pliers, which are often used concurrently with sutures to close wounds, crush the tissues of the lips of wound. Crushed tissues at a wound site prevent an adequate blood circulation to the wound site which harm its healing process.

The use of the sutureless wound closure device of the present invention results in a healed wound which is more resistant when subjected to tensiometric study and presents less scarring as opposed to wounds healed with sutures.

The sutureless wound closure device of the present invention allows for clinicians to have access to the wound easily and for the delivery of medication to the wound while the lips are held substantially closed by the device. Medication which can be used in accordance with the present invention includes any therapeutic agents, antibiotic, or antiseptic, among others.

Figure 2:
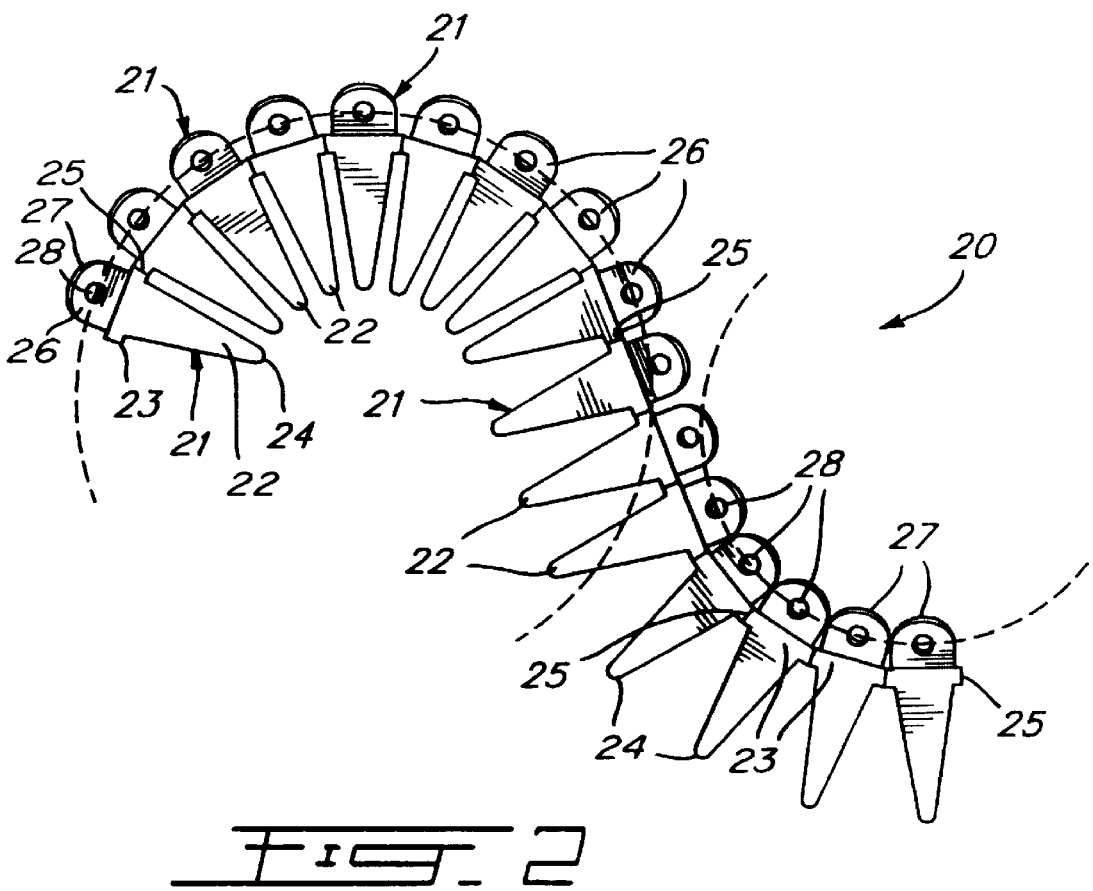
FIG. 2 is a top plan view of a first embodiment of a strip used in a sutureless wound closure device in accordance with the present invention.

Referring now to FIG. 2, there is shown a strip 20 for use with a similar strip 20 in a sutureless wound closure device in accordance with the present invention, the strip 20 comprising a plurality of similar anchor members 21 disposed side-by-side and each including an adhesive tail 22 and an eyelet 26 defining an opening 28 adapted to receive a thread, such as thread 30 of FIG. 3. Where the adhesive tail 22 merges with a corresponding eyelet 26, adjacent anchor members 21 are joined by a connecting portion 25.

The strip 20 is molded using a bio-compatible material such as silicon or rubber, or preferably by injection molding using an injectable polymer, such as polypropylene, polyethylene and more preferably high density polyethylene.

FIG. 2 also illustrates that the adhesive tails 22 each have a tapered shape with their wide end 23 being adjacent to the connecting portion 25 while their opposite end 24 is narrow. The tapered shape of the adhesive tails 22 allows for a flexibility of the strip 20 in three-dimension to follow the lips of wounds of any shape and, more particularly, the strip 20 can be positioned so as to follow a transversely curved wound, as seen in FIG. 2.

In FIG. 3, there is shown a first sutureless wound closure device D, in accordance with the present invention, which includes a pair of slightly modified strips 20a which are shown in operative position as being interconnected by the thread 30 engaging openings 28 of successive eyelets 26 while alternating between the two strips 20a. The difference between strip 20 of FIG. 2 and strip 20a of FIG. 3 resides in the shape and end width of the narrow outer ends 24/24a of the tails 22/22a of the anchor members 21/21a thereof.

The underface of the adhesive tails 22/22a is flat and is coated with a film of a strong bio-compatible adhesive to enable the tails 22/22a to be firmly adhered to the patient's skin S, as seen in FIG. 4. Such suitable bio-compatible adhesives include cyanomethacrylate, MASTISOL™ (Ferndale Laboratories Inc., Ferndale, Mich., 48220), and TUCK TAPE™ 406. Preferably, the strips 20/20a are affixed indirectly to the patient's skin S by being adhered on a self-adhesive non-woven fabric ULTRAFIX™ (sold by Dumex Medical Surgical Products Ltd., Scarborough, Ontario, Canada) or on a dressing retention sheet HYPAFIX™ (sold by Smith & Nephew Inc., Lachine, Quebec, Canada) previously adhered to the skin S, or any other equivalent tape may be used. In these instances, other suitable adhesives may be used, which may not necessarily be of bio-compatible grade. For packaging purposes the adhesive film of the adhesive tails 22/22a may be protected by a tear off cover sheet of non-adhering plastic material such as polyethylene, that is a cover sheet which, when removed from the strips 20/20a, is free of any adhesive as the adhesive is in fact retained on the strip 20/20a.

The eyelets 26 have a slightly tapered U-shaped plan outline, as shown in FIGS. 2 and 3, wherein the wider end merges to the connecting portion 25 and the narrow or rounded end corresponds to the inner or anchor end edge 27 (see FIG. 4). Each eyelet 26 is attached to an adjacent eyelet 26 along a small area, i.e. the connecting portion 25, thereby providing flexibility to the strip 20/20a.

The underface of the eyelets 26 is flat and may be coated with a film of a strong bio-compatible adhesive to enable the eyelets 26 to be firmly adhered to the patient's skin S directly or indirectly as described above for the tails 22.

Figure 5:
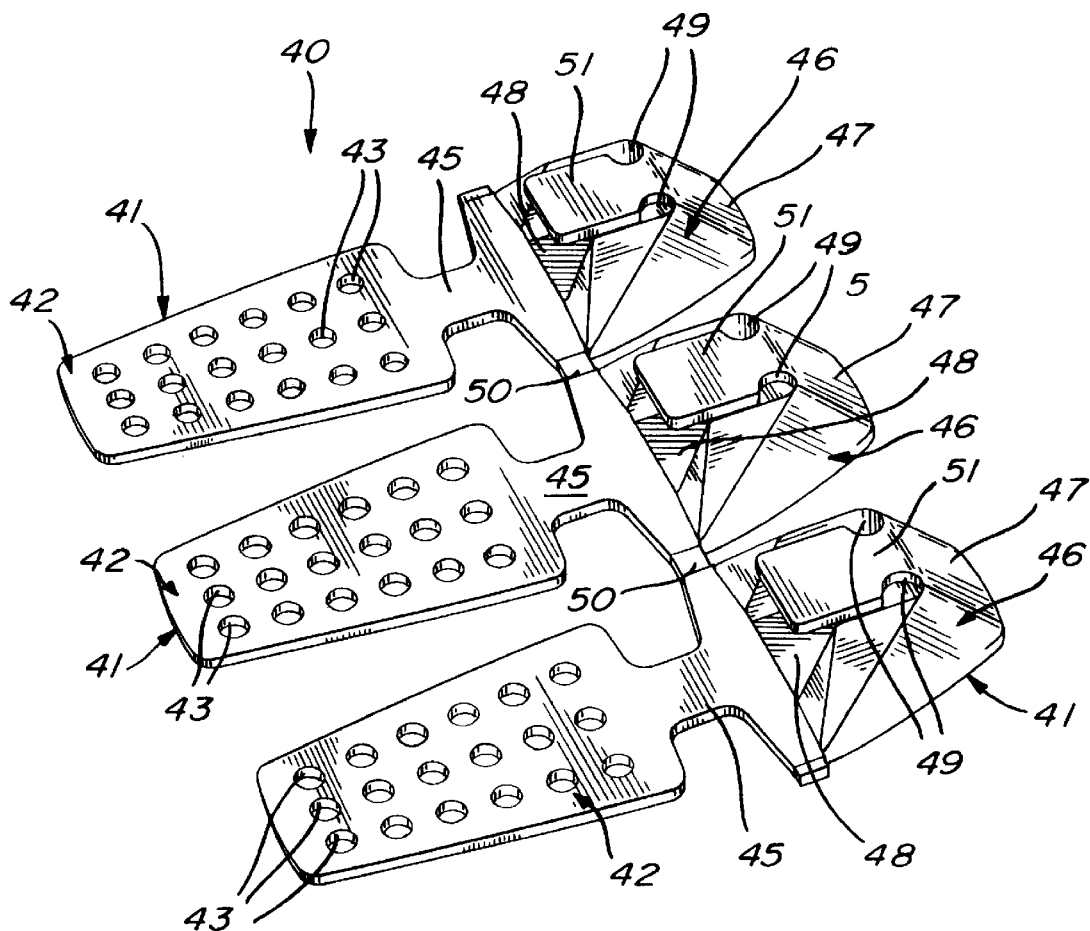
FIG. 5 is a perspective view of a portion of a third embodiment of a strip which is used in a second sutureless wound closure device in accordance with the present invention.

Now referring to FIG. 5, there is shown a third type of strip 40 for use with a similar strip 40 in a second sutureless wound closure device D' (see FIG. 6) in accordance with the present invention, the strip 40 comprising a plurality of similar anchor members 41 disposed side-by-side and each including an adhesive tail 42 and a hook member 46 defining a U-shaped opening 48 provided with a pair of inwardly projecting notches or recesses 49 at the inner ends thereof, wherein the opening 48 is adapted to receive a thread such as the thread 30 and the recesses 49 are adapted to retain the thread 30. The adhesive tails 42 merge with corresponding hook members 46 in respective anchor members 41 by connecting portions 45.

The adhesive tails 42 may be provided with perforations 43 closely spaced and extending longitudinally in parallel rows along the tails 42 and thus substantially transversely of the wound.

Figure 6:
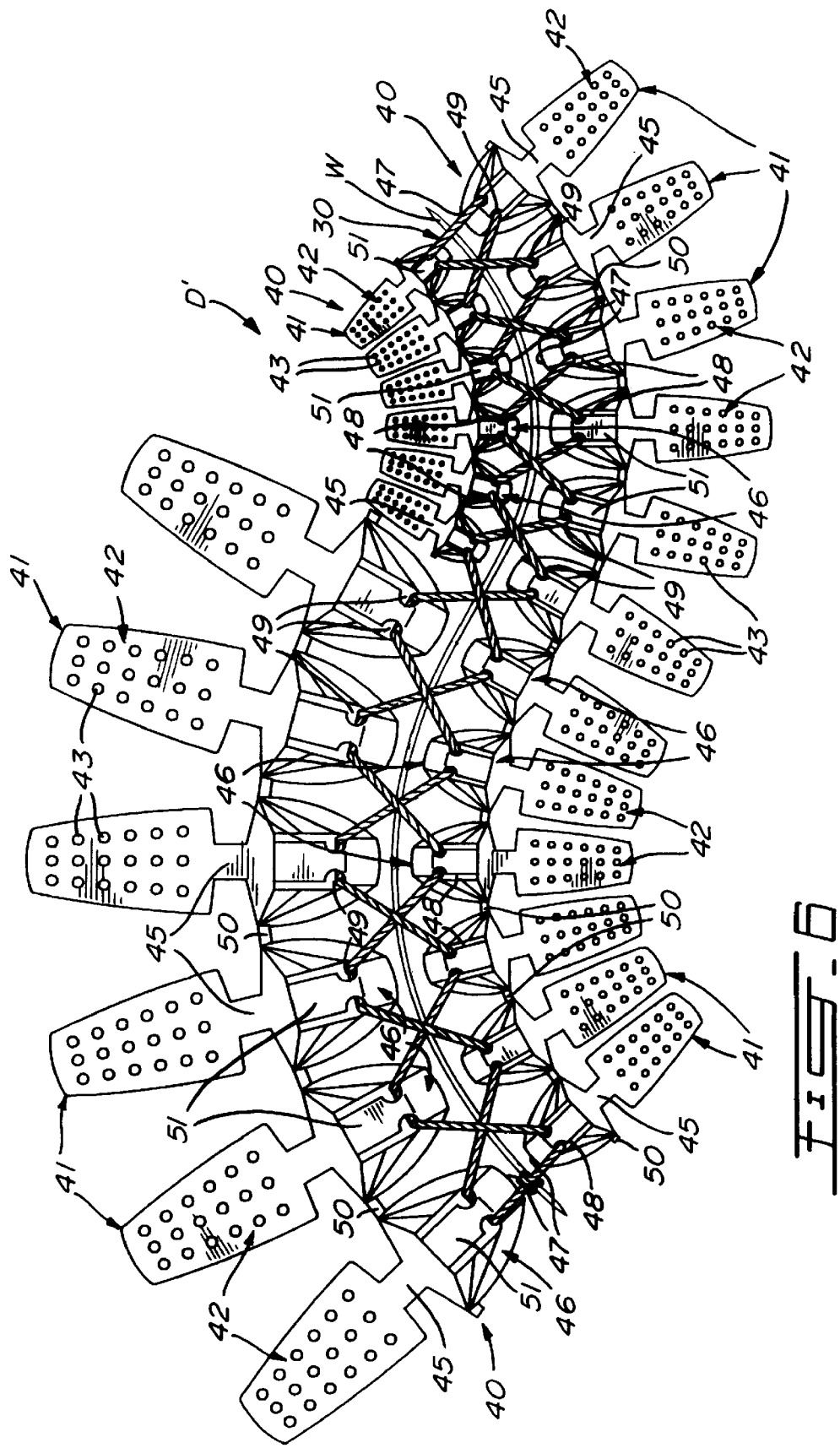
FIG. 6 is a top plan view of the second sutureless wound closure device of the present invention including a pair of third embodiment strips, as illustrated in part in FIG. 5, which are fastened together using a thread in a typical operative position.

The hook members 46 have a slightly tapered U-shaped plan outline, as shown in FIGS. 5 and 6, wherein the wider end merges with the connecting portion 45 and the narrow end corresponds to an inner or anchor end edge 47. Adjacent anchor members 41 are connected to one another at respective hook members 46 thereof along a small area 50 thereby providing the strip 40 with great flexibility.

Each hook member 46 has a thickness which tapers from the inner end edge 47 thereof outwardly towards the connecting portion 45. The opening 48 defines inwardly thereof an upper horizontal plateau-like member 51 which is vertically spaced apart from the rest of the hook member 46 as the latter is thinner at the outer end thereof (i.e. the end of the hood member which is adjacent to the connection portion 45), as shown in FIGS. 5 and 7, thereby defining a gap which allows the thread 30 to be engaged in the hook member 46, the thread 30 being then guided inwardly by the transversally oriented side arms of the U-shaped opening 48 until it securely nests in the recesses 49.

The underface of the tails 42 and the hook members 46 are flat and coated with a film of a strong bio-compatible adhesive to enable the tails 42 and the hook members 46 to be firmly adhered to the patient's skin directly or indirectly as described above for the tails 22 and eyelets 26 of FIGS. 2 to 4.

Figure 7:
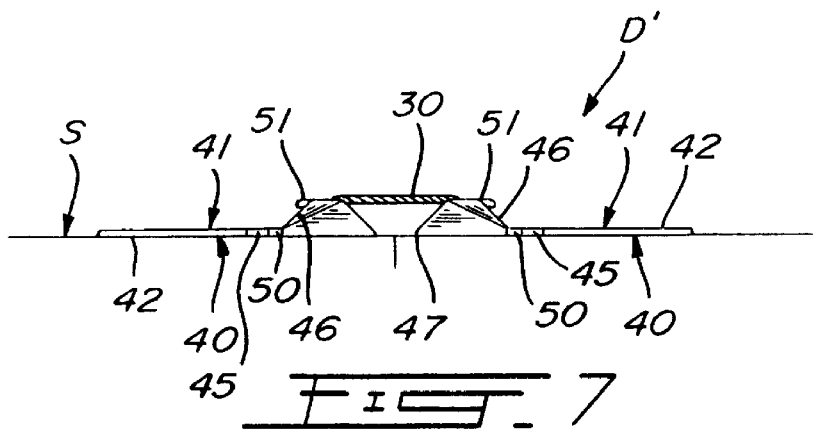
FIG. 7 is an end elevational view of the second sutureless wound closure device of FIG. 6.

FIGS. 6 and 7 illustrate the sutureless wound closure device D' which uses two strips 40 and the thread 30, in operative position on the patient's skin S.

The strips 20/20a and 40 are used as a substitute to sutures for wound closure in the following manner (FIGS. 4, 6, 7 and 8). A piece of a self-adhesive non-woven fabric ULTRAFIX™ or of a dressing retention sheet HYPAFIX™ is adhered to the patient's skin S adjacent to the lips of the wound and on each side thereof so as to cover the skin S. A first strip 20/20a or 40 is affixed over the non-woven fabric or the retention sheet on one side of the wound using the adhesive tails 22, 22a or 42 in order to have the eyelets 26 or the hook members 46 located in close proximity to the edge of the wound. A second similar strip 20, 20a or 40 is affixed in the same manner to the opposite side of the wound. Corresponding opposite eyelets 26 or hook members 46 of the strips 20, 20a or 40 are fastened together by the thread 30 which is passed through the openings 28 or 48 in a lacing fashion to secure and close the wound in a substantially constant tensiometric manner so that the lips of the wound are substantially equidistant from one another along the entire length of the wound. These strips 20, 20a and 40 allow for the closing of a wound without piercing the skin adjacent to the wound unlike sutures.

Figure 8:
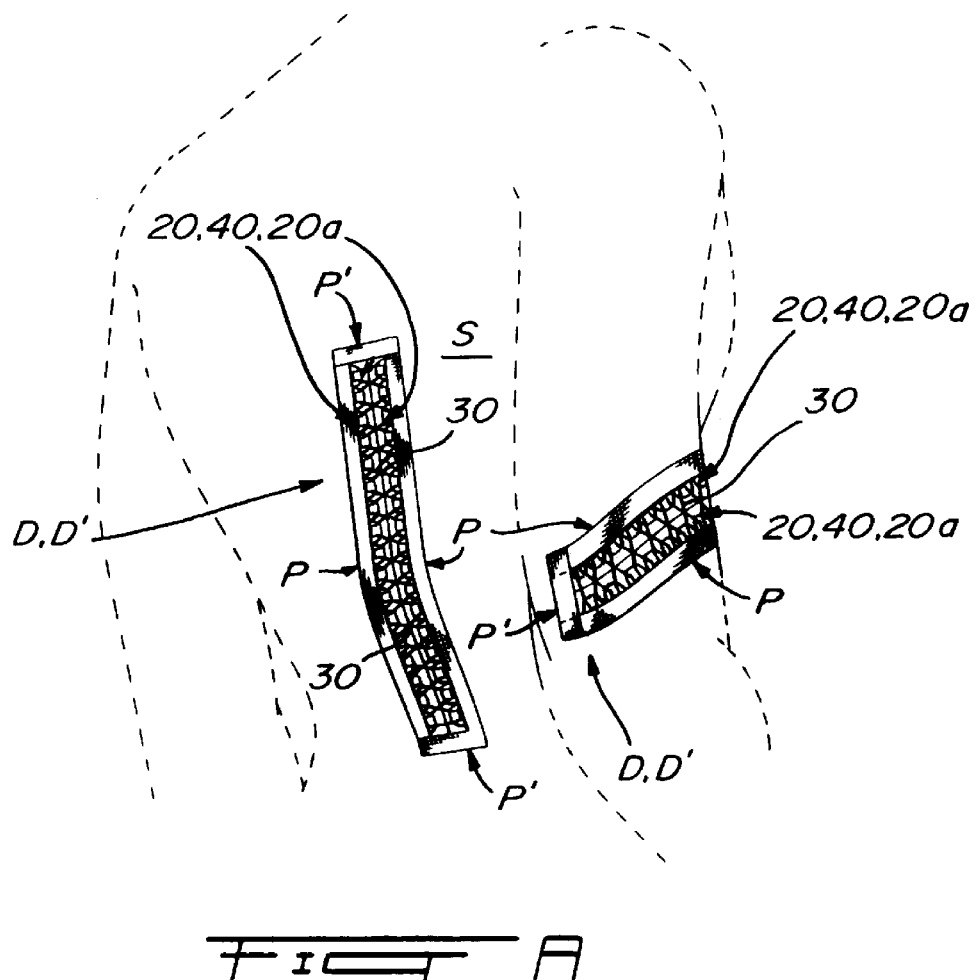
FIG. 8 illustrates a pair of the second sutureless wound closure devices of FIGS. 5 to 7 in typical operative positions on a patient.

As seen in FIG. 8, pieces P of a self-adhesive non-woven fabric ULTRAFIX™ or of a dressing retention sheet HYPAFIX™ may be used to longitudinally cover the tails 22, 22a or 42 on each side of the closed wound. Further similar pieces P' preferably can also be used to transversely cover the longitudinal ends of the wound closure devices D/D', as also illustrated in FIG. 8, thereby increasing the overall solidity of the assembly of the wound closure device D/D' with the self-adhesive non-woven fabric or the dressing retention sheet. Also, usual wound dressing or medication may be applied to the closed wound.

The tails 22, 22a and 42 and the eyelets 26 or hook members 46 all taper towards their respective free ends for allowing the strips 20, 20a and 40 to be laterally curved so as to follow transversely curved wounds (see FIGS. 2, 3 and 6).

With the angled eyelets 26 of FIG. 2 and of FIGS. 3 and 4 which receive the thread 30 through the openings 28 thereof at a distance above the plane of the patient's skin S, as well as with the U-shaped openings 48 and the recesses 49 of the hook members 46 of FIGS. 5 to 7 which also receive the thread 30 at a distance above the patient's skin S, the wound closure devices D and D' of the present invention ensure that the thread 30 remains spaced from the plane of the patient's skin and thus from the wound, even when the devices D/D' are curved in the plane of the wound (i.e. in a plane substantially perpendicular to the patient's skin S and extending between the pair of strips 21, 21a and 41) so as to follow a curvature of the patient's body. Indeed, the connection of the thread 30 with either wound closure devices D/D' takes place at a distance from the wound thereby preventing the thread from rubbing against the wound which would irritate the same and possibly infect it.

A typical strip 20, 20a or 40 in accordance with the first, second or third embodiments described hereinabove, has an overall length of 15 cm and a width of 2 cm for twenty anchor members 21, 21a or 41. The overall length and width depends on the size of the individual anchor members 21, 21a or 41. The smaller the anchor members 21, 21a or 41 are, the higher is the tensiometric pressure on the closing of the wound. Such a typical strip 20, 20a or 40 is usually sterilized and packaged in an individual wrapper and provided in sterile condition.

Furthermore, the anchor members 21, 21a and 41 are available in different widths in order that, when the wound closure device D or D' follows a wound curved sideways, that is a wound defining a curve which is not transversally linear (as in FIG. 6), various sizes of anchor members 21/21a/40 can be chosen so as to retain the face-to-face relationship of the anchor members of both strips disposed on each side of the curved wound. In other words, when the device D/D' follows a transversal curve as in FIG. 6, both strips 20, 20a or 40 have different radii of curvature along that curve with the inner strip having a smaller radius than the outer strip, whereby in order that the thread 30 follows a substantially constant pattern the inner strip will comprise anchor members 21, 21a or 41 of smaller width than that of the anchor members of the outer strip. This aspect of the present invention is well illustrated in FIG. 6. Therefore, the tensiometric pressure acting on the wound is substantially constant along the entire length thereof, even along various composite curves (i.e. curves transversal to the wound and/or in the plane of the wound, or a combination thereof) that the wound might define.

The sutureless wound closure devices D/D' of the present invention thus each includes two strips (20, 20a or 40) fastened together by the thread 30 to draw the anchor members 21/21a/41 of the respective strips towards one another so as to close an open wound extending therebetween. The device can therefore permit normal skin movements in the vicinity of the wound while, for the reasons explained above, preventing the two areas of skin adjacent to the wound from moving relative to one another thereby maintaining the lips of the wound substantially equidistant.

The present invention will be more readily understood by referring to the following examples which are given to illustrate the invention rather than to limit its scope.

EXAMPLE I

Comparative Tensiometric Study

Animals and wounds

Landrace x Yorkshire pigs (15 kg) were purchased from local producers in specific pathogen-free environment. They were housed in individual cages and fed ad libitum. Each experimental group contained 4 pigs. Wounds were performed as previously described by Garrel D. R. et al. (J. Surg. Res., 1991, 51:297–302). Briefly, four 6 cm-full-length cutaneous incision was made longitudinally on the dorsal skin of each pig under pentobarbital anesthesia.

Group 1

Two of the incisions were immediately closed with Dermalon 4.0™ sutures placed 1 cm apart on the left side of the back of the pigs.

Group 2

The incisions were immediately closed with the strips of the present invention placed at 0.2–0.5 cm on each side of the incision, laced and tightened on the right side of the back of the pigs.

Wound breaking strength

In this experiment, wound breaking strength was measured 3, 7 and 14 days post-injury. Pigs were sacrificed by lethal anesthesia, the dorsal skin of each pig was excised and cut into 3–4 strips, 1 cm wide by 5 cm long, with razor blades positioned onto a rigid support. Hemorrhaged or infected wounds were discarded. Each strip was placed between the clamps of a 1101 Instron™ tensometer and the amount of force (Newton) required to brake the strip was recorded. Tension was applied at 20 mm/min., and all measurements were done in a blind fashion.

As shown in Table 1, the device of the present invention (Group 2) resulted in a equivalence in wound strength as compared to sutures (Group 1).

Histological evaluation

On the day of the sacrificed one strip of each wound from this experiment was fixed in 10% formaldehyde, and later embedded in paraffin. Four-micrometer thick sections were stained with Hematein-Phloxin-Safran™ (HPS) and examined under light microscopy (Optiphot 2™ microscope, from Nikon).

Morphological evaluation includes aspect of the epidermis and of the cells within the scar, whereas morphometric evaluation includes thickness of the epidermis surrounding the scar, width of the scar at the level of both superficial and reticular dermis and cellularity, by counting fibroblasts per microscopic field, magnification×750.

Finally, some 2–5 µm-thick sections were stained with Sirius Red F3BA™ and examined under polarized light to evaluate the aspect of collagen within the scar.

Histological evaluation of the scars was conducted on wounded skin samples. At the epidermis level, the epithelium surrounding the scar was pluristratified, fully differentiated and keratinized in all treatment groups. Moreover, epidermis thickness was identical in all treatment groups (FIGS. 9A and 9B). At the dermis level, most of the cells within the scar were fibroblasts surrounded by collagen. When stained with Sirius Red™, collagen fibers within the scar were shown to be unorganized and of smaller diameter when compared to those of normal dermis.

TABLE 1

Wound strength

| Source of Variation | DF | SS | MS | F | P |
|---|---|---|---|---|---|
| Day | 2 | 1.11 | 5536.01 | 4.52 | <0.001 |
| Treatment | 1 | 2.41 | 2.41 | 0.20 | 0.660 |
| Day x Treatment | 2 | 17.04 | 8.52 | 0.70 | 0.505 |
| Residual | 37 | 453.49 | 12.26 | — | — |
| Total | 42 | 1.15 | 274.56 | — | — |

DF = degrees of freedom
SS = sums of squares
MS = mean squares
F = F statistic (F test)
P = probability (P value)

The differences in the mean values among the different levels of day are greater than would be expected by chance after allowing for the effects of differences in treatment. There is a statistically significant difference (P<0.001). To isolate which group(s) differ from the others, a multiple comparison procedure is used.

The differences in the mean values among the different levels of treatment are not great enough to exclude the possibility that the difference is just due to random sampling variability after allowing fro the effects of differences in treatment. There is not a statistically significant difference (P=0.660).

The effect of different levels of day does not depend on what level of treatment is present. There is not a statistically significant interaction between day and treatment (P=0.505).

The two-way analysis of variance, with treatment (sutures v. harness of the present invention) and day (3, 7 and 14 days) as factors, has resulted in the effect of day where P<0.001 and the effect of treatment where P=0.660 and the interaction of day×treatment where P=0.505. Thus, the strength of wound after 3, 7 and 14 days are equivalent for both sutures and the harness of the present invention.

Thus, the device of the present invention increased wound breaking strength in vivo. This effect was not associated with increased scar width and cellularity. In all observed histological sections, no sign of inflammation, of cheloid or of tumoral foci could be detected.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

I claim:

1. A device for closing a cutaneous wound comprising at least two three-dimensionally flexible strips for placement at opposite sides of the wound, each step comprising a plurality of anchor members disposed side-by-side, each anchor member comprising a tail portion and a head portion wherein adjacent anchor members of each strip are attached to one another by a three-dimensionally flexible connecting portion disposed intermediate distal ends of the tail portion and the head portion of the anchor members, wherein said tail portion has a larger end and a smaller end wherein the anchor members of each strip are capable of detachable securement to the skin of a patient along a side of the wound such that the head portions of each strip extend inwardly toward the wound, wherein each head portion includes an engagement means for permitting adjustable laced attachment with the head portion of the strip disposed on the opposite side of the wound without contacting the wound, wherein the strips are capable of being drawn toward each other, whereby the lips of the wound are drawn toward each other while the strips remain spaced apart.

2. The device of claim 1, wherein said anchor members are dimensioned for exerting a substantially constant tensiometric pressure substantially along the entire length of the wound, the lips of the wound being substantially equidistant from one another.

3. The device of claim 2, wherein for a transversely curved wound said device must substantially follow the curved wound thereby requiring that said device be also transversely curved, whereby said anchor members of any strip to be located on the inside of the curved wound are of smaller width than opposite anchor members of any strip to be located on the outside of the curved wound.

4. The device of claim 1, wherein said head and tail portions taper from said connecting portion respectively towards the distal ends of said anchor members, whereby said strip can be transversely curved on one side thereof up to a minimum inner radius wherein said inner elements abut each other, and on an opposite side thereof up to a minimum outer radius wherein said outer elements abut each other.

5. The device of claim 1, wherein said anchor members are elongated and are adapted to extend substantially at right angles to the wound and in at least one plane substantially coplanar to at least one general plane of the skin adjacent to the wound, said anchor members comprising adhesive means on at least part of an underside thereof.

6. The device of claim 5, wherein the head portion of each anchor member further comprises a thread receiving and retaining means.

7. The device of claim 6, wherein said tail portion comprises an adhesive on a lower surface thereof.

8. The device of claim 6, wherein said tail portion defines a series of perforations.

9. The device of claim 6, wherein said thread receiving and retaining means comprises an adhesive on a lower surface thereof.

10. The device of claim 1, wherein said anchor members each comprise thread receiving and retaining means adapted to maintain a thread, when said device is in an operative position, at a distance from the wound.

11. The device of claim 10, wherein said lace receiving and retaining means comprise hook means at an end of said lace receiving and retaining means opposite another end thereof adapted to be in close proximity to the skin.

12. The device of claim 11, wherein said hook means comprise a retaining member dependent at an inner end thereof from said lace receiving and retaining means and extending therefrom in a direction substantially opposite to the wound, said hook means also comprising a substantially U-shaped opening defined substantially around and under said retaining member and oriented substantially inwardly, ends of said opening being adjacent to said inner end of said retaining member and defining thereat inwardly facing notch means for retaining the lace means in said operative position.

13. The device of claim 12, wherein a vertical gap is defined between an outer end of said retaining member and a lower section of said lace receiving and retaining means for allowing the lace means to be inserted under the retaining member for subsequent displacement thereof towards said notch means.

14. The device of claim 1, further comprising tape means for removable attachment to the skin adjacent each side of the wound, said strips being adapted to be secured to said tape means on a side thereof opposite the skin.

15. The device of claim 14, wherein there is provided further tape means for positioning at least partly over said strips for further securing said device to said tape means.

16. The device of claim 1, wherein said members of both said strips are interconnected to each other by the thread in such a way that said device, in an operative position thereof, is three-dimensionally flexible, while retaining said strips and thus the lips of the wound substantially equidistant.

17. The device of claim 1, wherein each said anchor member defines a U-shaped opening including a retention recess at each inner end of said U-shaped opening, wherein said U-shaped opening is adapted to receive a thread and said retention recess is adapted to retain the thread so received in said anchor member.

18. The device according to claim 1 further comprising an attachment means disposed between the bottom surface of the tail portions and the skin of the patient for releasably securing respective strips around the wound.

19. The device according to claim 1 further comprising at least one ligature for mutually securing at least two head portions disposed on opposite sides of the wound.

20. The device according to claim 19 wherein the engagement means comprises means for supporting the ligature above the surface of the wound.

21. The device according to claim 1 wherein the head portions of the strips are tapered inwardly.

22. A device for closing a cutaneous wound comprising at least two three-dimensionally flexible strips for placement at opposite sides of the wound, each strip comprising a plurality of anchor members disposed side-by-side and each including a tail portion and a head portions said tail portion having a larger end and a smaller end each anchor member comprising engagement means, wherein adjacent anchor members of each strip are attached to one another by a three-dimensionally flexible connecting portion, wherein the anchor members of each strip are capable of detachable securement to the skin of a patient along a side of the wound, wherein a single lace means is provided for permitting adjustable laced attachment between engagement means on both sides of the wound without contacting the wound, wherein the strips are capable of being drawn toward each other by said lace means, whereby the lips of the wound are drawn toward each other while the strips remain spaced apart.

23. A device for closing a cutaneous wound comprising at least two three-dimensionally flexible strips for placement at opposite sides of the wound, each strip comprising a plurality of elongated anchor members disposed side-by-side, each anchor member comprising a tail portion and a head portion, said tail portion having a larger end and a smaller end, wherein adjacent anchor members of each strip are attached to one another by a three-dimensionally flexible connecting portion disposed intermediate distal ends of the tail portion and the head portion of the anchor members, wherein the anchor members of each strip are capable of detachable securement to the skin of a patient along a side of the wound, wherein said connecting portions permit adjacent head portions of a same strip to be distanced or brought closer together such that the head portions of each strip extend inwardly toward the wound with each anchor member extending substantially transversely to the wound, wherein each anchor member includes an engagement means for permitting adjustable laced attachment with the anchor member of the strip disposed on the opposite side of the wound without contacting the wound, wherein the strips are capable of being drawn toward each other, whereby the lips of the wound are drawn toward each other while the strips reman spaced apart.

* * * * *